US012575943B1

(12) United States Patent
Frasca et al.

(10) Patent No.: US 12,575,943 B1
(45) Date of Patent: Mar. 17, 2026

(54) LOCKING SWIVEL PATELLA CLAMP

(71) Applicant: GLOBUS MEDICAL, INC., Audubon, PA (US)

(72) Inventors: Ryan Frasca, Phoenixville, PA (US); Jason Zappacosta, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/889,707

(22) Filed: Sep. 19, 2024

(51) Int. Cl.
*A61F 2/46* (2006.01)

(52) U.S. Cl.
CPC ...... *A61F 2/461* (2013.01); *A61F 2002/4622* (2013.01); *A61F 2002/4625* (2013.01); *A61F 2002/4687* (2013.01)

(58) Field of Classification Search
CPC .............. A61F 2/461; A61F 2002/4622; A61F 2002/4625; A61F 2002/4687
See application file for complete search history.

(56) References Cited

U.S. PATENT DOCUMENTS

| | | | | |
|---|---|---|---|---|
| 5,002,547 A * | 3/1991 | Poggie | .................... | A61F 2/461 |
| | | | | 606/88 |
| 5,941,884 A * | 8/1999 | Corvelli | ............. | A61B 17/1767 |
| | | | | 606/88 |
| 6,010,509 A * | 1/2000 | Delgado | ................. | A61F 2/461 |
| | | | | 606/88 |
| 9,078,676 B2 * | 7/2015 | Randle | ............... | A61B 17/1767 |
| 10,945,765 B2 * | 3/2021 | Miller | ................. | A61B 17/645 |

* cited by examiner

*Primary Examiner* — Tracy L Kamikawa

(57) ABSTRACT

A patella clamp includes a lockable swivel that is able to freely tilt from 1° to 30° in any direction and then be locked in that orientation. This ability to freely swivel will allow a user to align a resected surface of a patella parallel to the other end of the patella clamp to make the operative surfaces of the implant and the patella substantially parallel to each other.

17 Claims, 6 Drawing Sheets

LOCKING SWIVEL PATELLA CLAMP

FIELD

This disclosure relates to clamps used in surgical procedures, in general, and to patella clamps, in particular.

BACKGROUND

Resurfacing of the patella is a surgical procedure in which the surgeon removes the articular surface of the patella and replaces it with a patella implant. According to certain procedures, the surgeon resects the articular surface of the patella to create a substantially flat, resected surface thereon. In certain procedures, generally, the resected surface may be further prepared for receiving the contemplated patella implant by drilling peg holes or similar receiving portions into the resected surface.

Subsequent to preparation of the resected surface, various additional steps are taken to implant the desired patella implant. In certain procedures, known as cemented procedures, the resected surface may be coated with a suitable cement and thereafter the patella implant may be pressed onto the coated surface. A patella clamp may be used in such cement-related procedures.

Other procedures may not rely primarily on cement or may not use cement at all. Such cementless procedures generally involve the patella implant or similar patellar component being clamped into place, generally by a patella clamp.

Patella clamps of the current art may benefit from certain modifications or improvements. For example, it is oftentimes desirable to accommodate variable anatomical geometry, especially that associated with the patella on its non-resected side, during clamping engagement between the patella implant and the resected side of the patella. It is likewise valuable to distribute clamping force evenly to ensure the resected surface has full or optimal contact with the opposing surface of the patella implant.

SUMMARY

In one suitable implementation, this disclosure relates to a patella clamp that has a first, patella side, which may be used to engage a patella during a resurfacing operation. In particular, the clamp may engage the non-resected surface of the patella, with the resected surface thereof generally oriented in the opposite direction from the engaged non-resected surface. The patella clamp has a second implant side opposite the patella side of the clamp. The implant side of the clamp is able to hold a patella implant during associated clamping operations between the patella implant and the resected surface of the patella. To accommodate the sometimes asymmetrical and varying geometries of patellas of different patients, especially uneven surfaces of the non-resected side engaged by the patella clamp, the patella clamp features a lockable swivel connected to the patella side of the clamp.

In certain implementations, the patella side of the clamp makes use of a jaw, and the lockable swivel is connected to this jaw. The lockable swivel, in turn, is movably retained and received in a dish likewise located at the patella side of the clamp. A spiked plate is connected to the lockable swivel for engaging the non-resected side of the patella thereon.

A retaining ring is rotatably interconnected between the swivel and the spiked plate to permit selective rotation of the spiked plate relative to the swivel itself. The patella clamp, according to certain implementations, includes a locking pin which is selectively actuatable to lock the swivel relative to the aforementioned dish. The locking pin may be moved between an unlocked position and a locked position. In the unlocked position, the locking pin slidably retains the swivel relative to the dish. In the locked position, the locking pin fixes the swivel relative to the dish. As such, the patella, when received on the spiked plate, may be tilted to a desired orientation so that the resected surface of the patella is aligned parallel to an opposing surface of the patella implant received on the patella side of the clamp.

In still further implementations, the swivel is operable by moving it relative to the dish by having the locking pin slidably received in a swivel aperture extending through a convex, pivoting surface of the swivel. The convex, pivoting surface of the swivel, in turn, opposes a corresponding concave surface of the dish. A portion of the locking pin is received in the swivel aperture and slidably retains the swivel when in the unlocked position and engages edges of the swivel aperture when the locking pin is brought into the locked position.

In certain implementations, the swivel aperture may be in the form of a star-shaped cut-out, the cut-out having a center and arms dimensioned to slidably receive the locking pin therein. The arms of the star-shaped cut-out extend radially outwardly from the center through predetermined arcs. As such, a plurality of user-selectable fixation points are made possible for the swivel.

In still other implementations, the star-shaped cut-out has seven arms, each of the arms extending in predetermined arcs of 30° from the center. Such arrangement allows a user to selectably tilt the spiked plate from 1° to 30° when the swivel is moved relative to the locking pin from the center of the cut-out to the end of one of the arcs of the arms.

In still further implementations, the retaining ring allows rotation of the spiked plate regardless of how the swivel has been tilted and regardless of to what fixation point the swivel has been affixed.

According to certain methods associated with this disclosure, a method of clamping a patella implant to a resected surface of a patella is disclosed for use in association with a resurfacing procedure. In one possible method under this disclosure, the articular surface of the patella implant is received so as to position its porous surface along a first reference plane. A patella is engaged by its non-resected surface and such engagement positions the resected surface of the patella along a second reference plane. As such, the orientation of the porous surface of the patella implant and the orientation of the resected surface of the patella correspond to the respective first and second planes. According to this implementation, if it is determined that the first and second reference planes are at different orientations to each other, that is, the opposing surfaces are not parallel, the method involves swiveling the engaged patella to a position that aligns the associated second reference plane of the resected patella surface to the first reference plane of the porous surface of the patella implant.

In this way, clamping engagement may proceed by moving the patella implant and the patella relatively toward each other through applying inwardly directed force through the patella clamp and maintaining parallel alignment of the first and second reference planes during such procedure.

BRIEF DESCRIPTION OF THE DRAWINGS

A more complete understanding of the present disclosure, and the attendant advantages and features thereof, will be readily understood by reference to the following detailed description, when considered in conjunction with the accompanying drawings, wherein.

DETAILED DESCRIPTION

One possible implementation of a patella clamp 21 according to the present disclosure is illustrated in FIGS. 1-8. Patella clamp 21 includes a lockable swivel 27 on a patella side 23 of clamp 21, such patella side opposite a patella implant side 25 adapted to receive a patella implant i thereon. As detailed herein, lockable swivel 27 is configured to be able to selectively rotate to any direction in terms of the 360° of arc or compass points associated with a spiked plate on which patella p is engaged, and is likewise able to selectively tilt or swivel to an angle selected from a suitable range of angles in relation to the orientation of a reference plane associated with an engagement surface on which patella implant i has been received.

Figure 1:
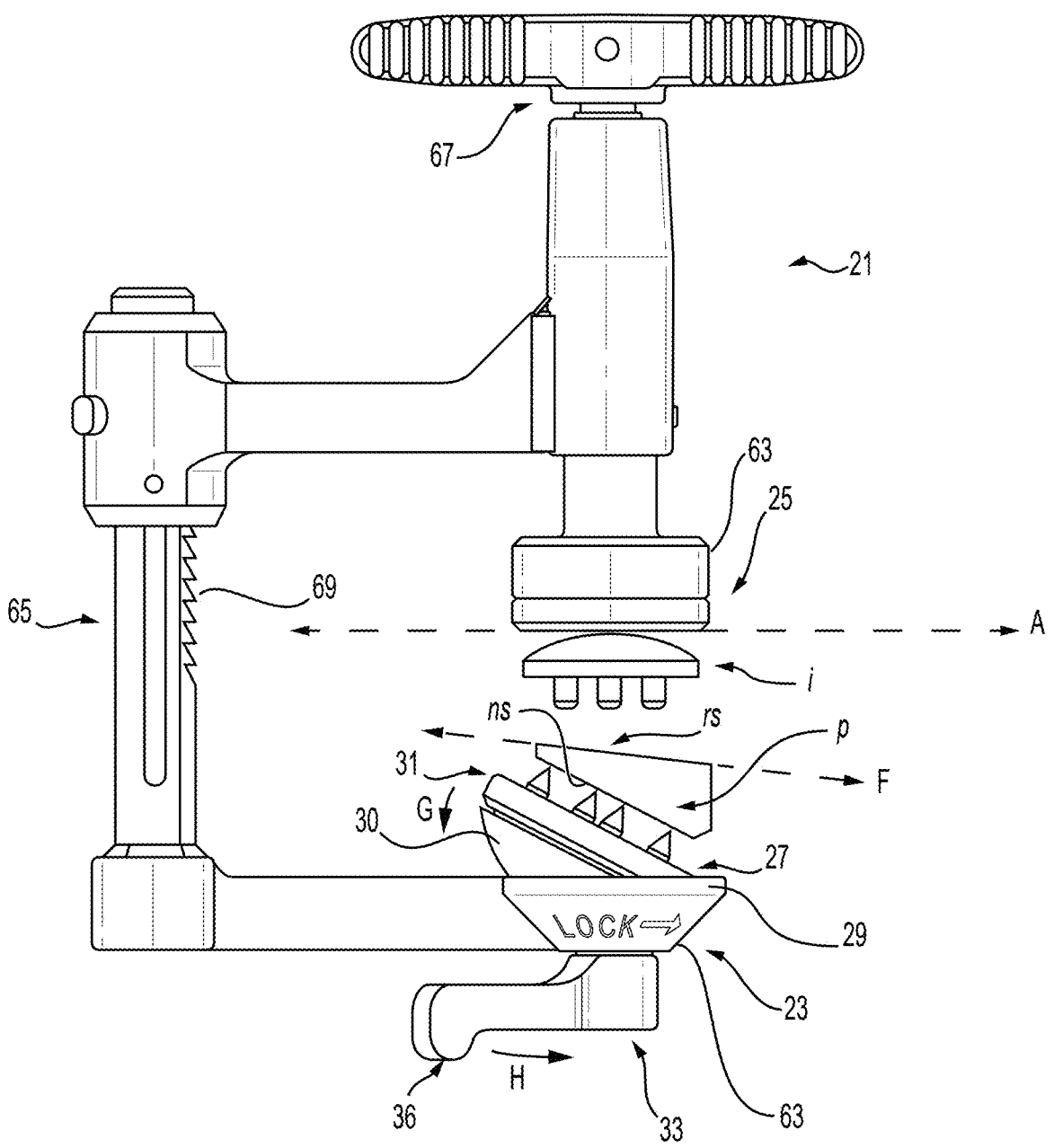
FIG. 1 is a side, elevational view of a patella clamp according to one possible implementation of the present disclosure.
Figure 2:
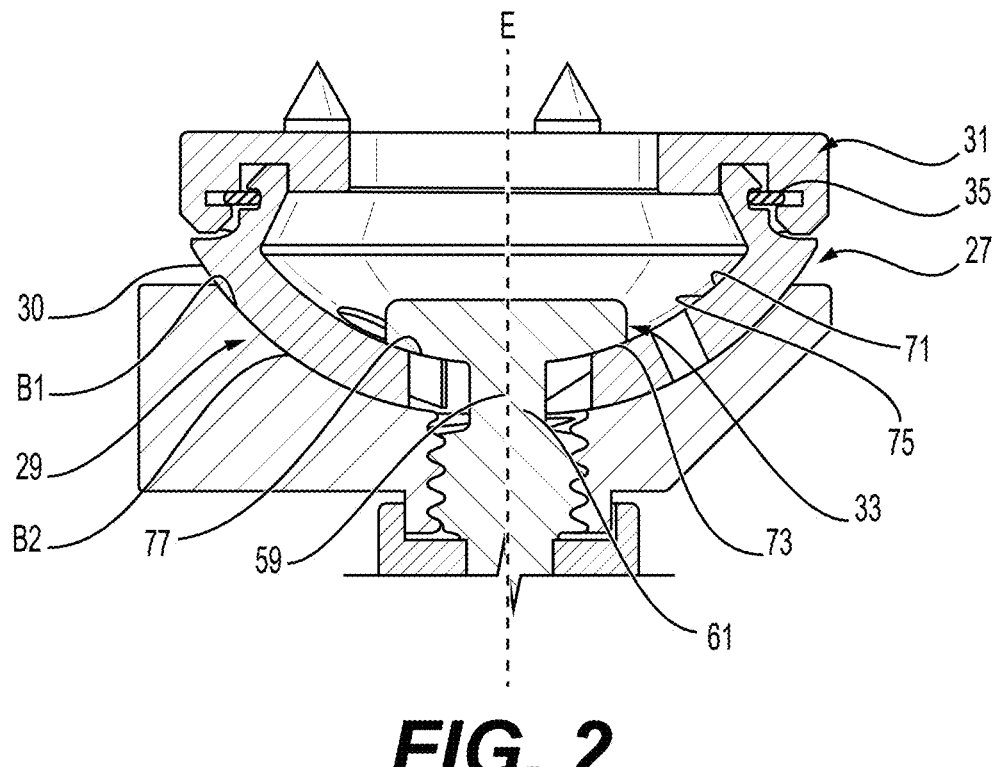
FIG. 2 is a side, cross-sectional view of a patella side of a patella clamp according to an aspect of the present disclosure.

The user may thus initiate rotation and/or tilting or swiveling in any direction and may then selectively lock swivel 27 in a selected angular orientation in the selected direction. This ability to readily, selectively, or freely tilt or swivel, potentially in combination with selective rotation, will allow the user, such as a surgeon, to set the resected surface rs of patella p parallel to a contemplated engagement surface of a patella implant i received on the opposite side of the clamp, that is, patella implant side 25 (FIG. 1). Thereafter, patella clamp 21 may be suitable operated to move patella implant i and patella p relatively toward each other and into clamping engagement by applying suitable, inwardly directed force.

In one suitable implementation, lockable swivel 27 is received in a dish 29 formed at patella side 23. Dish 29 has a concave surface 37 and lockable swivel 27 has a corresponding convex, pivoting surface 30 opposing the concave surface 37 of dish 29. Dish 29 has a bore 41 defined in concave surface 37, whereas pivoting surface 30 has a swivel aperture 43 aligned with bore 41.

A locking pin 33 is operatively connected to the dish 29 and swivel 27, so as to be actuatable between an unlocked position and a locked position. The unlocked position slidably retains swivel 27 relative to dish 29 so that a user may selectively tilt swivel 27 relative to dish 29 to a desired position, whereas the locked position permits the user to fix swivel 27 at the selected position relative to the other components of patella clamp 21, such as dish 29. In the illustrated implementation, locking pin 33 has a locking pin shaft 45 extending through bore 41 and swivel aperture 43 and terminating in a locking pin head 47. Locking pin head 47 has a portion extending transversely relative to locking pin shaft 45 to define a flange 49.

A retaining ring 35 is rotatably interconnected between swivel 27 and a spiked plate 31 against which the non-resected ns side of patella p is engaged. The rotatable interconnection permits rotating of spiked plate 31 in combination with the aforementioned tilting of swivel 27 to a desired angle in any of the 360° of arc defined relative to reference plane A of patella clamp 21.

Figure 5:
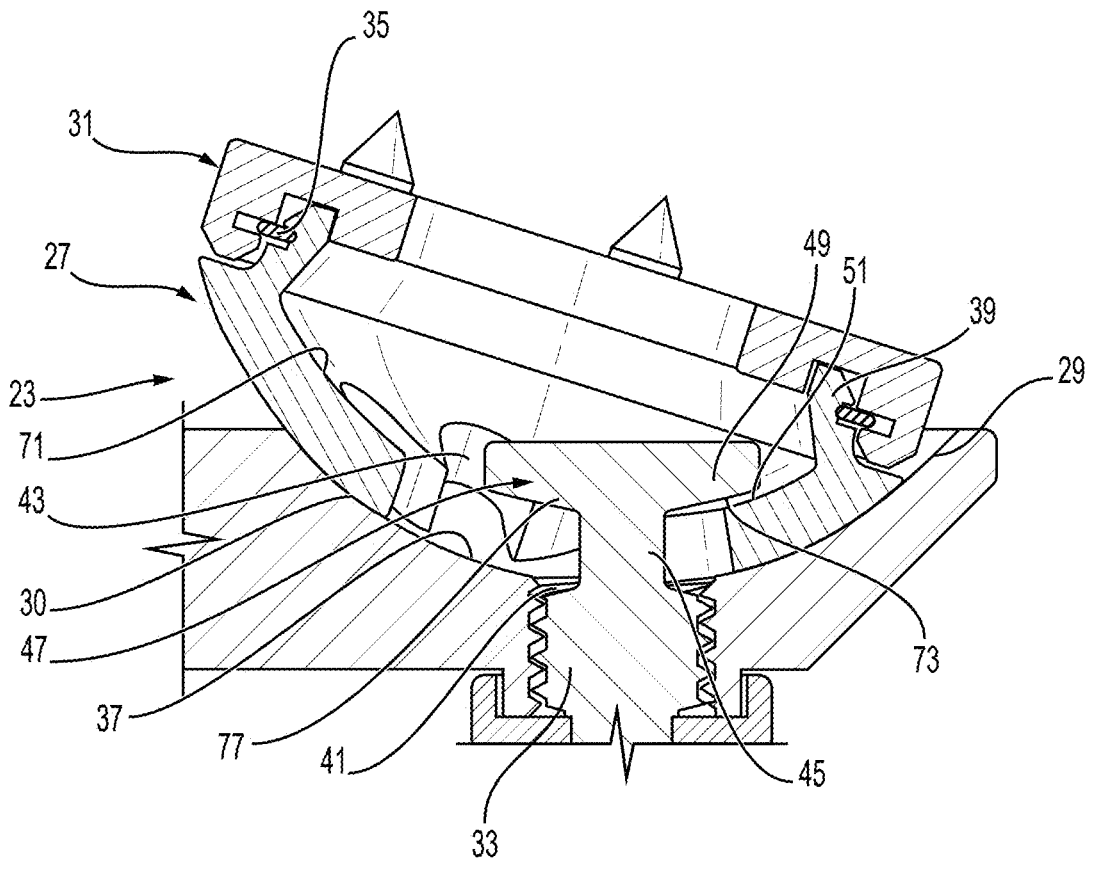
FIG. 5 is a side, cross-sectional view of the patella side of the patella clamp shown in FIG. 1.
Figure 6:
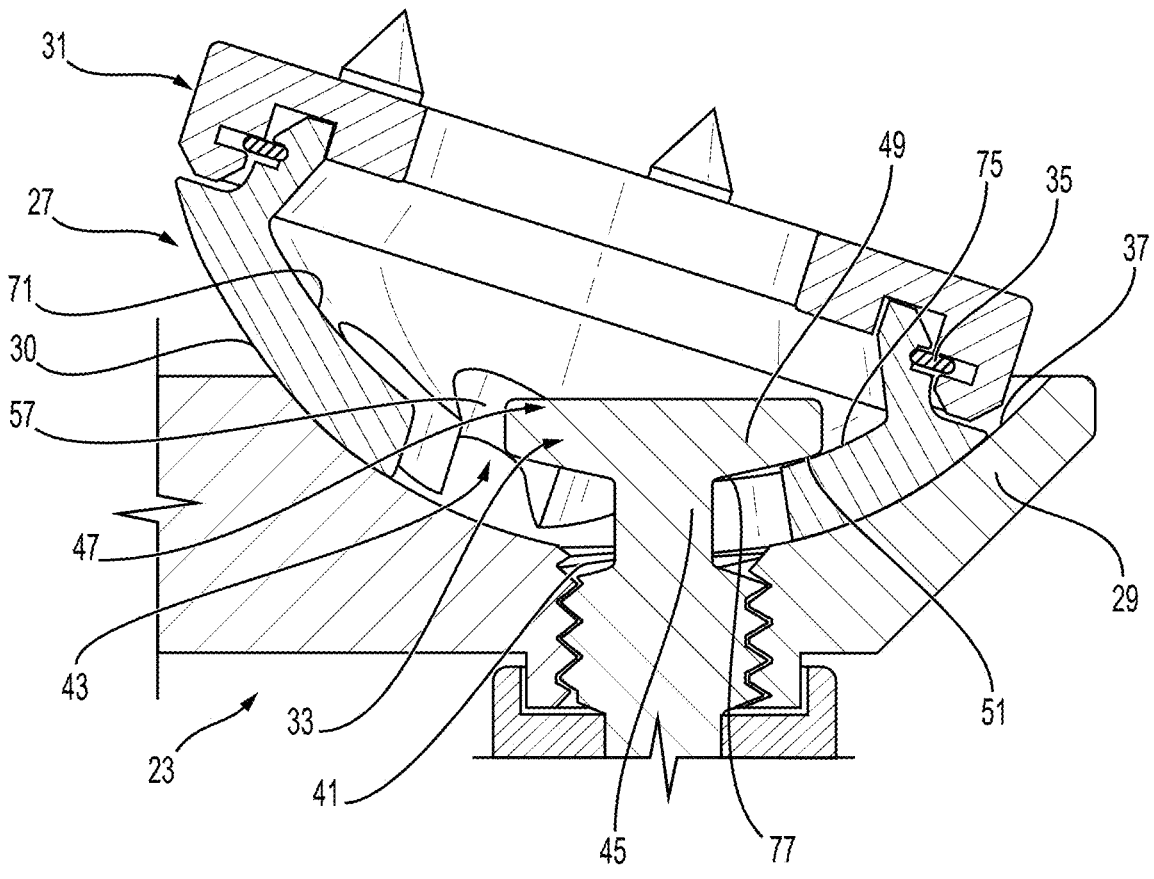
FIG. 6 is another side, cross-sectional view of the patella side of the patella clamp shown in FIG. 1, with the locking pin in the locked state.
Figure 7:
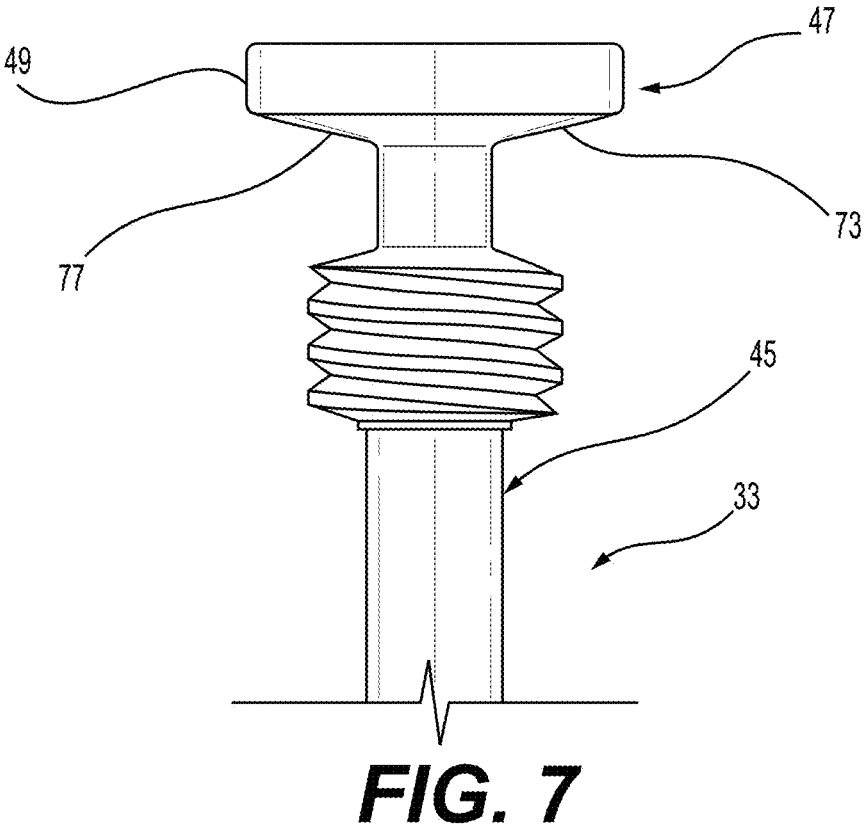
FIG. 7 is a side, elevational view of one possible implementation of a locking pin according to the present disclosure.
Figure 8:
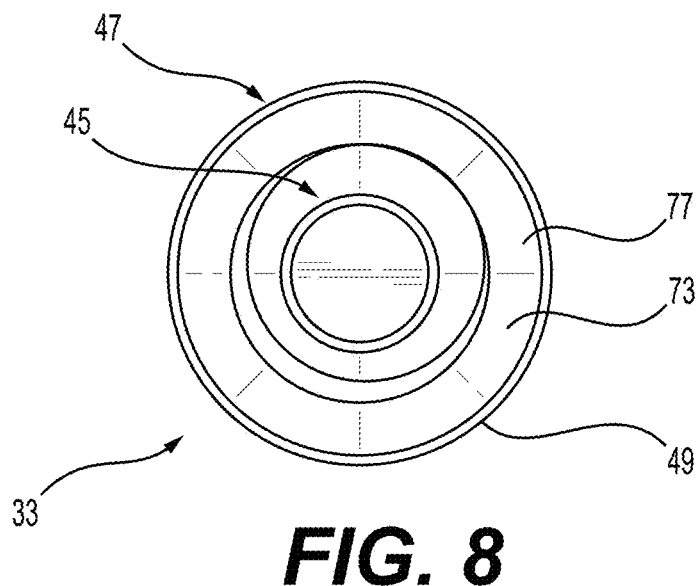
FIG. 8 is a bottom, plan view of the implementation of FIG. 7.

Swivel aperture 43 is defined by swivel aperture edges 51, such edges extending in at least one direction over a distance greater than the diameter of locking pin shaft 45 and less than at least one dimension of flange 49. In such configuration, flange 49 may engage swivel aperture edges 51 when locking pin 33 is in the locked position. As best seen in FIG. 5, when in the unlocked position, locking pin permits swivel 27 to slide relative to dish 29 to a user-selectable orientation. Such orientation may correspond to the orientation of patella implant i and be achieved by user-selected motion of swivel aperture 43 relative to locking pin shaft 45 received therein.

Figure 3:
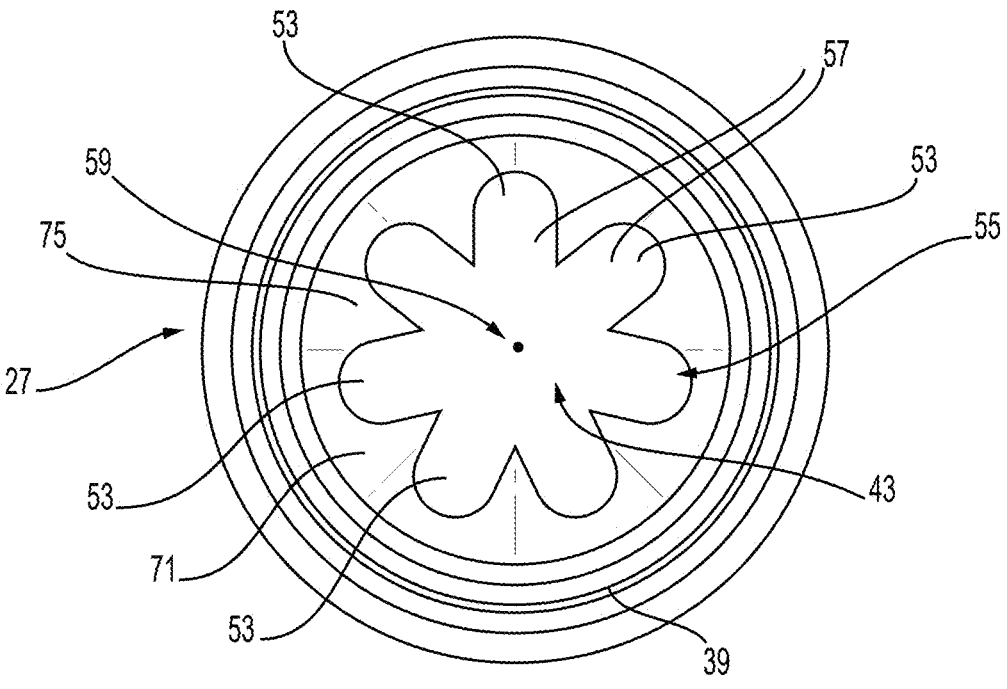
FIG. 3 is a top, plan view of a swivel for a patella clamp according to certain implementations of the present disclosure.
Figure 4:
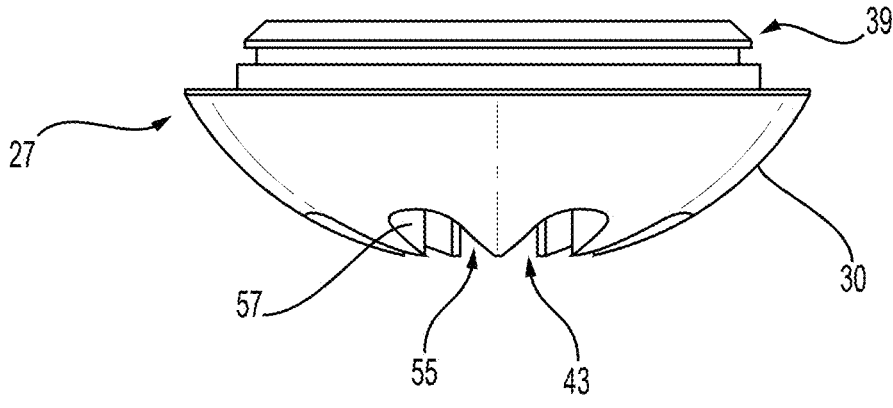
FIG. 4 is a side elevational view of the swivel of FIG. 3.

The dimensions and shape of swivel aperture 43 may be varied in terms of any number of parameters to meet any number of desired functional properties, including the amount of tilt and the availability of tilt in any number of angles of rotation of spiked plate 31 relative to the patella implant side 23 of patella clamp 21. In the illustrated implantation, pivoting surface 30 may tilt from 0° to 30° of tilt relative to the reference plane A. As best seen in FIGS. 3 and 4, swivel aperture 43 comprises a star-shaped cut-out 55 having a center 59 and arms 57 radiating outwardly from center 59. Arms 57 are dimensioned to form slots 53 to slidably receive the locking pin shaft 45 therein. Although any number of arms 57 may be suitable. The illustrated implementation comprises seven of the arms 57, so, alternately, if there are only two of the arms 57 radiating at 180° from each other, swivel aperture 43 will be in the form of a single slot 53 sized to slidably receive the locking pin shaft 45 therein. As such, the number and configurations of arms 57 or corresponding slots 53 may vary from a single slot 53 to seven slots 53 or arms 57 as illustrated.

Still further variations in terms of numbers and orientations of slots arms 57, or still other configurations of swivel aperture 43 are within the scope of this disclosure. For example, if limited tilting were desirable, swivel aperture 43 may be a circle or polygon having a diameter sufficiently large to be received through swivel aperture 43 but smaller than the outer diameter of flange 49, such that portions of flange 49 may nonetheless engage edge portions of the circular or polygon form of swivel aperture 43 when in their un-tilted, 0° position, bore 41 and the center 59 of star-shaped cutout 55 are centered along longitudinal axis E at respective base points 61 of pivoting surface 30 and concave surface 37 of dish 29. Arms 57 extend through predetermined arcs and define a locus of user selectable fixation points at which swivel 27 may be tilted by a user seeking at least one fixation point that orients swivel 27 and spiked plate 31 (on which patella p may be received) at a desired position relative to reference plane A, such as aligned to be parallel with such reference plane A. In this manner, when patella p is received on the spiked plate 31, resected surface rs of patella p is aligned parallel to an opposing surface of the patella implant i when received on the patella implant side 25 of clamp 21 (FIG. 1).

In still further implementations, the swivel is operable by moving it relative to the dish by having the locking pin slidably received in a swivel aperture extending through a convex, pivoting surface of the swivel. The convex, pivoting surface of the swivel, in turn, opposed a corresponding concave surface of the dish. A portion of the locking pin is received in the swivel aperture and slidably retains the swivel when in the unlocked position and engages edges of the swivel aperture when the locking pin is brought into the locked position.

Patella clamp 21 includes opposing clamp jaws 63, one disposed at patella side 23 of clamp 21 and the other disposed at patella implant side 25 oriented to be in spaced relation to jaw 63 on the patella side 23. The two jaws 63 are interconnected by a C-shaped frame 65. Jaws 63 are moveable relative to each other by any suitable means, in this case a screw 67 and a ratchet 69. Either or both of jaws 63 may be selectively operated to move patella implant i relative to resected surface rs of patella p disposed on the opposite one of clamp jaws 63. The jaws may likewise be retracted relative to each other by the same or similar means.

In addition, with swivel 27 unlocked the unresected surface of the resected patella can be placed on the spiked plate. An inward force can be applied closing the clamp and bringing the implant engaging surface into contact with the resected surface of the patella. This forces plane F to become parallel to plane A. The swivel can then be locked in this orientation using handle 36. The clamp can now be opened bringing the implant engaging surface away from the now parallel resected patella surface. The patella implant can now be placed against the implant engaging surface and clamped into place as the resected surface of the patella has already been set and locked parallel to the porous surface of the patellar implant.

Referring more particularly to FIG. 2, 5-8, swivel 27 is formed with an inner, swivel surface 71 disposed opposite pivoting surface 30 of swivel 27. Flange 49 extends from locking pin shaft 45 radially outwardly in multiple, radial directions, in this case to define a circular flange surface 73 opposing inner, swivel surface 71. This configuration allows flange surface 73 to be selectively engageable against inner swivel surface 71 across substantially the entire area of flange surface 73. Such contact urges pivoting surface 30 against concave surface 37 of dish 29 to affix the relative positions of swivel 27 and dish 29 and thereby affix spiked plate 31 at a desired orientation.

Although the opposing inner swivel surface 71 and flange surface 73 may assume any number of forms, in the illustrated implementation, inner swivel surface 71 comprises a concave portion 75 and flange surface 73 comprises an opposing, mating convex portion 77 to accomplish the aforesaid engagement of swivel 27 and dish 29.

The various operations and functions of the patella clamp 21 of the present disclosure are readily apparent from the foregoing description. In one suitable method, patella implant i is clamped to a resected surface rs of patella p which is being resurfaced in association with a resurfacing procedure. The patella implant side 25 of patella clamp 21 receives an articular surface of patella implant i to position a porous surface of the implant along a first reference plane corresponding to the orientation of the porous surface of the patella (for example, reference plane A, FIG. 1). Opposite patella implant side 25, that is, on patella side 23 of clamp 21, patella p is engaged to position a resected surface rs of patella p along a second reference plane F corresponding to the orientation of the resected surface rs of the patella p. If it is determined that the first and second reference planes correspond to different orientations, that is, the resected surface of the patella is not parallel to the porous surface of the patella implant, then swiveling of the engaged patella p may be accomplished by suitable tilting and other user manipulations disclosed herein of swivel 27 until the swivel is positioned to align the second reference plane F parallel to the first reference plane A. As illustrated, tilting or swiveling of swivel 27 in the direction of arrow G may produce the desired alignment.

After the foregoing alignment step and the associate determination that the first and second reference planes are parallel to each other, locking pin 33 is suitably actuated, in this case by rotating a user accessible handle 36 in the direction of the LOCK indicia show in FIG. 1, thereby engaging patella p at the corresponding swiveled, position.

Once the desired relative orientation of resected surface rs of patella p and the porous surface of patella implant i have been achieved, suitable operations of ratchet 69, screw 67 or other clamping mechanisms of patella clamp 21 are actuated to move patella implant i and resected surface rs of patella p relatively toward each other. Continued inward movement results in clamping engagement by applying suitable, inwardly directed force. Maintaining parallel alignment of the first and second reference planes A and F during the foregoing clamping engagement operation optimizes even placement of patella implant i onto resected surface rs of patella p.

The foregoing alignment of the operative surface of patella implant i and the opposing surface of patella p has thus been achieved by swiveling or tilting the swivel 27 to an angular position of between 1° and 30° relative to the reference plane of porous surface of patella implant I, optionally rotating spiked plate 31 relative to patella implant I, and locking the swivel 27 in such position.

The flexibility and variability of the foregoing swiveling step may be accompanied by rotating spiked plate 31 relative to dish 29 and pivoting surface 30 by means of retaining ring 35.

Various potential advantages are apparent from the foregoing description. As one potential advantage, patella clamp 21 is able to accommodate a wide variety of patient anatomy by tilting and/or rotating the patella relative to the patella implant i and locking it in such position to ensure that resected surface rs of the patella p is held parallel to patella implant i located on the patella implant side 25 of clamp 21.

This has a further advantage that implant i will be seated more easily in an optimal position.

Such ease of operation, in turn, improves surgical workflow by reducing the amount of delay in properly affixing patella clamp 21 to its associated patella implant i and patella p.

By holding patella p in an improved orientation for implant insertion, patient outcomes are likewise optimized and efficient operation of patella clamp 21 is made easier.

It will be further understood that various changes in the details, materials, and arrangements of the components disclosed herein may be made by those skilled in the art without departing from the spirit and scope of the present disclosure. Furthermore, one skilled in the art would appreciate that the illustrated and disclosed embodiments and variations thereof are non-limiting. It will also be appreciated that one or more features may be omitted from one or more other alternative embodiments without departing from the scope of the disclosure as expressed in the claims appended hereto.

What is claimed is:

1. A patella clamp, comprising:

first and second jaws, the first jaw adapted to engage a non-resected surface of a patella, the second jaw located opposite the first jaw and moveable relative thereto, the second jaw adapted to engage a patella implant configured to be clamped to a resected surface of the patella at a corresponding orientation relative to a reference plane;

a lockable swivel connected to the first jaw of the clamp;

a dish into which the lockable swivel is received;

a spiked plate connected to the lockable swivel;

a locking pin selectively actuatable to lock the lockable swivel relative to the dish;

a retaining ring rotatably interconnected between the lockable swivel and the spiked plate to permit selective rotation of the spiked plate relative to the lockable swivel;

wherein the locking pin is moveable between an unlocked position and a locked position, the unlocked position slidably retaining the lockable swivel relative to the dish and the locked position fixing the lockable swivel relative to the dish;

wherein the lockable swivel comprises a star-shaped cut-out, the star-shaped cut-out having a center and arms dimensioned to slidably receive the locking pin therein, the arms extend radially outwardly from the center through predetermined arcs to define a locus of user-selectable fixation points on the lockable swivel, at least one of the fixation points orienting the lockable swivel and the spiked plate at a desired orientation relative to the reference plane, whereby when the patella is received on the spiked plate, the resected surface of the patella is configured to be aligned parallel to an opposing surface of the patella implant when received on the second jaw.

2. The patella clamp of claim 1, wherein the star-shaped cut-out comprises seven of the arms, each of the arms extending in a predetermined arc of 30° from the center to permit user selectable tilt of the spiked plate from 1° to 30° when the lockable swivel is moved relative to the locking pin such that the locking pin moves from the center of the star-shaped cut-out to an end of the arc of one of the arms.

3. The patella clamp of claim 1, wherein the retaining ring is adapted to permit rotation of the spiked plate when fixed at any of the user-selectable fixation points.

4. The patella clamp of claim 1, wherein the dish has a concave surface; and wherein the lockable swivel has a corresponding convex, pivoting surface opposing the concave surface.

5. The patella clamp of claim 1, wherein the locking pin comprises a flange having a convex portion, and the lockable swivel has a concave surface adapted to mate with the convex portion of the flange when in the locked position, thereby fixing the lockable swivel and the spiked plate at the desired orientation.

6. In a patella clamp having a patella side adapted to engage a non-resected surface of a patella and having a patella implant side opposite the patella side and moveable relative thereto, the patella implant side adapted to engage a patella implant configured to be clamped to a resected surface of the patella, at a corresponding orientation relative to a reference plane, the improvement to the patella clamp comprising:

a lockable swivel connected to the patella side of the clamp;

a dish into which the lockable swivel is received;

a spiked plate connected to the lockable swivel;

a locking pin selectively actuatable to lock the lockable swivel relative to the dish;

a retaining ring rotatably interconnected between the lockable swivel and the spiked plate to permit selective rotation of the spiked plate relative to the lockable swivel;

wherein the dish has a concave surface;

wherein the lockable swivel has a corresponding convex, pivoting surface opposing the concave surface;

wherein the locking pin is moveable between an unlocked position and a locked position, the unlocked position slidably retaining the lockable swivel relative to the dish and the locked position fixing the lockable swivel relative to the dish;

wherein the lockable swivel extends to a circumferential edge;

wherein the spiked plate is rotatably mounted to, and oriented outwardly from, the circumferential edge of the lockable swivel and is configured to be selectively engageable with the non-resected surface of the patella;

wherein the dish has a bore defined in the concave surface and the pivoting surface has a swivel aperture aligned with the bore;

wherein the locking pin has a locking pin shaft extending through the bore and the swivel aperture and terminating in a locking pin head, the locking pin head having a portion extending transversely relative to the locking pin shaft to define a flange;

wherein the swivel aperture is defined by edges, the edges extending in at least one direction over a distance greater than a diameter of the locking pin shaft and less than at least one dimension of the flange, so that the edges of the swivel aperture are engageable by the flange;

wherein the locking pin is further adapted so that, when in the unlocked position, the lockable swivel is slidable to a user-selectable orientation corresponding to an orientation of the patella implant by moving the swivel aperture relative to the locking pin shaft received therethrough; and wherein, the locking pin is further adapted so that when in the locked position, the lockable swivel is configured to be fixed in the user-selectable orientation.

7. The improved patella clamp of claim 6, wherein the swivel aperture comprises at least one slot sized to slidably receive the locking pin shaft therein and to permit the flange to be engageable with portions of the edges of the slot.

8. The improved patella clamp of claim 6, wherein the swivel aperture comprises a star-shaped cut-out having arms radiating outwardly from a center, wherein the arms are dimensioned to slidably receive the locking pin shaft therein.

9. The improved patella clamp of claim 8, wherein the pivoting surface and the opposing concave surface, when in an un-tilted position, define respective base points located at the center of the swivel aperture and aligned with the bore.

10. The improved patella clamp of claim 9, wherein the center of the star-shaped cut-out is located at the base point of the pivoting surface of the lockable swivel, selective movement of the locking pin shaft from the center of the star-shaped cut-out into one of the arms configured to cause a corresponding tilting of the lockable swivel and the spiked plate relative to the reference plane.

11. The improved patella clamp of claim 10, wherein the arms extend radially from the center through predetermined arcs to define a locus of user-selectable fixation points on the lockable swivel, at least one of the fixation points orienting the lockable swivel and the spiked plate relative to the reference plane, whereby when the patella is received on the spiked plate, the resected surface of the patella is configured to be aligned parallel to an opposing surface of the patella implant when received on the patella implant side.

12. The improved patella clamp of claim 11, wherein the predetermined arc of each of the arms extends 30° from the center to permit user selectable tilt of the spiked plate from 1° to 30° when the lockable swivel is moved relative to the locking pin such that the locking pin moves from the center of the star-shaped cut-out to an end of the arc of one of the arms.

13. The improved patella clamp of claim 12, wherein the star-shaped cut-out comprises seven of the arms.

14. The improved patella clamp of claim 12, wherein the retaining ring is adapted to permit rotation of the spiked plate when fixed at any of the user-selectable fixation points.

15. The improved patella clamp of claim 6, comprising a first jaw disposed on one of the sides of the clamp and a second jaw disposed on the other of the sides of the clamp, the first and second jaws opposing each other and interconnected by a C-shaped frame, the frame having at least one of a screw and a ratchet connected to at least one of the first and second jaws to advance and retract the first and second jaws relative to each other.

16. The improved patella clamp of claim 6,
wherein the lockable swivel comprises an inner, swivel surface opposite the pivoting surface;
wherein the flange extends from the locking pin shaft radially outwardly in multiple, radial directions to define a flange surface opposing the inner, swivel surface;
wherein the flange surface is located to be selectively engageable against the inner, swivel surface to urge the pivoting surface of the lockable swivel against the concave surface of the dish and affix the spiked plate at a desired orientation; and
wherein the flange surface is located to be selectively disengageable from the inner, swivel surface to permit slidable movement of the pivoting surface relative to the concave surface of the dish.

17. The improved patella clamp of claim 16,
wherein the inner, swivel surface comprises a concave portion; and
wherein the flange surface comprises an opposing, mating convex portion.

* * * * *